(12) United States Patent
Fujikura

(10) Patent No.: US 10,209,203 B2
(45) Date of Patent: Feb. 19, 2019

(54) WAFER INSPECTION APPARATUS AND WAFER INSPECTION METHOD

(71) Applicant: SUMITOMO CHEMICAL COMPANY, LIMITED, Tokyo (JP)

(72) Inventor: Hajime Fujikura, Ibaraki (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 66 days.

(21) Appl. No.: 15/405,605

(22) Filed: Jan. 13, 2017

(65) Prior Publication Data

US 2017/0131219 A1    May 11, 2017

Related U.S. Application Data

(63) Continuation of application No. PCT/JP2015/069668, filed on Jul. 8, 2015.

(30) Foreign Application Priority Data

Jul. 14, 2014    (JP) ................. 2014-144062

(51) Int. Cl.
*G06K 9/00* (2006.01)
*G01N 21/95* (2006.01)
(Continued)

(52) U.S. Cl.
CPC ......... *G01N 21/9501* (2013.01); *G01N 21/94* (2013.01); *G01N 21/956* (2013.01);
(Continued)

(58) Field of Classification Search
CPC .......... G01N 21/9501; G01N 21/8806; G01N 21/956; G01N 21/47; G01N 2021/8887;
(Continued)

(56) References Cited

U.S. PATENT DOCUMENTS 4,601,577 A    7/1986 Gotou et al.
5,274,434 A    12/1993 Morioka et al.
(Continued)

FOREIGN PATENT DOCUMENTS

JP    59-135353 A    8/1984
JP    9-105618 A    4/1997
(Continued)

OTHER PUBLICATIONS

Extended European Search Report, dated Jun. 16, 2017, for European Application No. 15822847.8.
(Continued)

*Primary Examiner* — Li Liu
(74) *Attorney, Agent, or Firm* — Birch, Stewart, Kolasch & Birch, LLP

(57) ABSTRACT

A wafer inspection apparatus including a light emitter configured to emit light onto a to-be-inspected surface of a wafer, an imaging unit configured to obtain an image formed by the light emitted from the light emitter and reflected by the to-be-inspected surface, a moving unit configured to move a to-be-inspected position on the to-be-inspected surface by controlling a position of one of the wafer and the light emitter, and an inspecting unit configured to inspect the to-be-inspected surface by detecting a scatter image formed by the light that is emitted from the light emitter and scattered by a defect of the to-be-inspected surface, where the scatter image is formed outside an outline of the image formed by the light emitted from the light emitter.

10 Claims, 9 Drawing Sheets

(51) Int. Cl.
*G01N 21/956* (2006.01)
*G06T 7/00* (2017.01)
*G01N 21/94* (2006.01)

(52) U.S. Cl.
CPC ........ *G06T 7/0004* (2013.01); *G01N 2201/02* (2013.01); *G01N 2223/634* (2013.01); *G06T 2207/30148* (2013.01)

(58) Field of Classification Search
CPC ......... G06T 2207/30148; G06T 7/0004; G06T 7/0002
See application file for complete search history.

(56) References Cited

U.S. PATENT DOCUMENTS

| | | | | |
|---|---|---|---|---|
| 5,293,538 | A * | 3/1994 | Iwata | G01N 21/8806 356/239.1 |
| 5,801,824 | A | 9/1998 | Henley | |
| 6,381,356 | B1 * | 4/2002 | Murakami | G01N 21/9501 257/E21.53 |
| 6,774,991 | B1 * | 8/2004 | Danko | G01N 21/95623 250/559.41 |
| 7,126,699 | B1 * | 10/2006 | Wihl | G01B 11/0608 356/625 |
| 7,623,229 | B1 * | 11/2009 | Vaez-Iravani | G01N 21/9501 356/237.4 |
| 9,207,188 | B2 * | 12/2015 | Terreno | G01N 21/9515 |
| 2002/0186368 | A1 | 12/2002 | Rosengaus et al. | |
| 2004/0179193 | A1 | 9/2004 | Maezono et al. | |
| 2007/0076195 | A1 * | 4/2007 | Yamaguchi | G01N 21/8806 356/237.1 |
| 2009/0147248 | A1 | 6/2009 | Kohayase et al. | |

FOREIGN PATENT DOCUMENTS

| | | |
|---|---|---|
| JP | 2001-349716 A | 12/2001 |
| JP | 2004-212353 A | 7/2004 |
| JP | 2009-283633 A | 12/2009 |
| JP | 2012-13632 A | 1/2012 |
| WO | WO 03/005007 A1 | 1/2003 |

OTHER PUBLICATIONS

European Office Action, dated Dec. 5, 2017, for European Application No. 15822847.8.
Japanese Notification of Reasons for Refusal, dated Dec. 5, 2017, for corresponding Japanese Application No. 2014-144062, with an English machine translation.
International Search Report for PCT/JP2015/069668 (PCT/ISA/210) dated Oct. 13, 2015.
Japanese Notification of Reasons for Refusal (including an English translation thereof) issued in the corresponding Japanese Patent Application No. 2014-144062 dated Jun. 26, 2018.

* cited by examiner

WAFER INSPECTION APPARATUS AND WAFER INSPECTION METHOD

CROSS REFERENCE TO RELATED APPLICATIONS

This application is a Continuation of PCT International Application No. PCT/JP2015/069668, filed on Jul. 8, 2015, which claims priority under 35 U.S.C. § 119(a) to Patent Application No. 2014-144062, filed in Japan on Jul. 14, 2014, all of which are hereby expressly incorporated by reference into the present application.

BACKGROUND

1. Technical Field

The present invention relates to a wafer inspection apparatus and a wafer inspection method.

2. Related Art

For the purposes of evaluating the quality of wafers, the deposition environment provided by apparatuses designed to deposit predetermined films on wafers and the like, inspection has conventionally been conducted to, for example, detect defects present on to-be-inspected surfaces of wafers. Such inspection is performed using apparatuses such as an apparatuses equipped with an optical microscope and an apparatus that emits light from a light source to obtain images of the entire to-be-inspected surfaces of wafers (see, for example, Japanese Patent Application Publications Nos. 2009-283633 and 2012-13632).

The inspection apparatus using an optical microscope as disclosed in Japanese Patent Application Publication No. 2009-283633 may be only capable of inspecting part of the to-be-inspected surface. In other words, the apparatus may not be capable of inspecting the entire to-be-inspected surface. Accordingly, the apparatus cannot obtain the information regarding the defects that may be present in the not-inspected region of the to-be-inspected surface and thus cannot accurately inspect the to-be-inspected surface. If a spot laser, which is configured to emit spot-like laser light, is used as the light source as disclosed in Japanese Patent Application Publication No. 2012-13632, the spot-like laser light needs to be scanned across the entire to-be-inspected surface in order to inspect the entire to-be-inspected surface. This may increase the time required to complete the measurement.

In light of the above, the objective of the present invention is to solve the above-described problems and accurately inspect wafers within a short period of time.

SUMMARY

One aspect of the present invention provides a wafer inspection apparatus including a light emitter configured to emit light onto a to-be-inspected surface of a wafer, an imaging unit configured to obtain an image formed by the light emitted from the light emitter and reflected by the to-be-inspected surface, a moving unit configured to move a to-be-inspected position on the to-be-inspected surface by controlling a position of one of the wafer and the light emitter, and an inspecting unit configured to inspect the to-be-inspected surface by detecting a scatter image formed by the light that is emitted from the light emitter and scattered by a defect of the to-be-inspected surface, where the scatter image is formed outside an outline of the image formed by the light emitted from the light emitter.

Another aspect of the present invention provides a wafer inspection method including causing a light emitter to emit light onto a to-be-inspecting surface of a wafer and causing an imaging unit to obtain an image formed by the light emitted from the light emitter and reflected by the to-be-inspected surface, moving a to-be-inspected position on the to-be-inspected surface by controlling a position of one of the wafer and the light emitter, and inspecting the to-be-inspected surface by detecting a scatter image formed by the light that is emitted from the light emitter and scattered by a defect of the to-be-inspected surface, where the scatter image is formed outside an outline of the image formed by the light emitted from the light emitter. Here, the obtaining of the image and the moving are repeatedly performed until the entire to-be-inspected surface is inspected.

According to the present invention, wafers can be inspected accurately within a short period of time.

EXEMPLARY EMBODIMENTS OF THE INVENTION

<One Embodiment>

(1) Structure of Wafer Inspection Apparatus

The following describes a wafer inspection apparatus relating to one embodiment mainly with reference to FIGS. 1A to 5.

(Light Emitter)

Figure 1A:
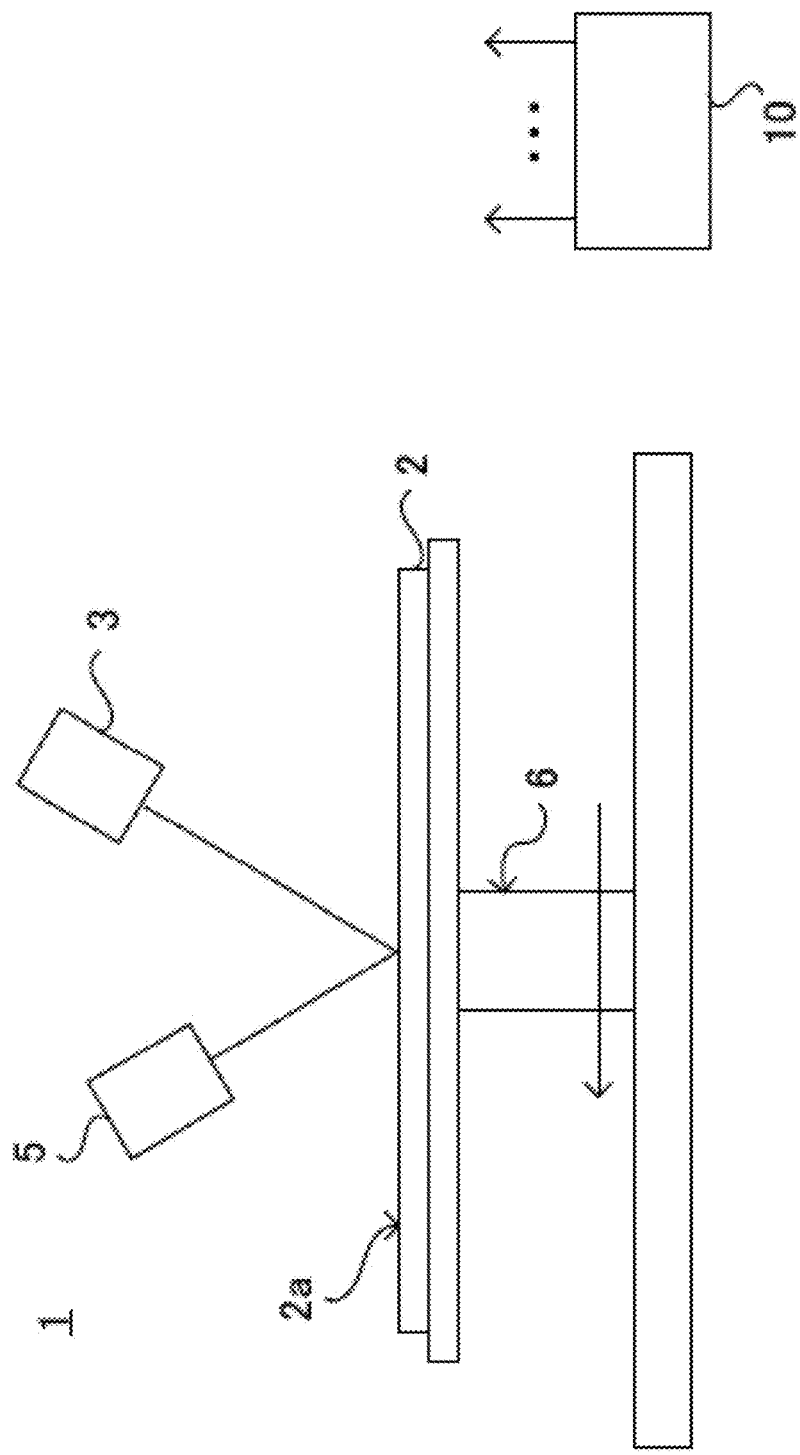
FIG. 1A is a vertical cross-sectional view schematically showing the structure of a wafer inspection apparatus relating to one embodiment.
Figure 1B:
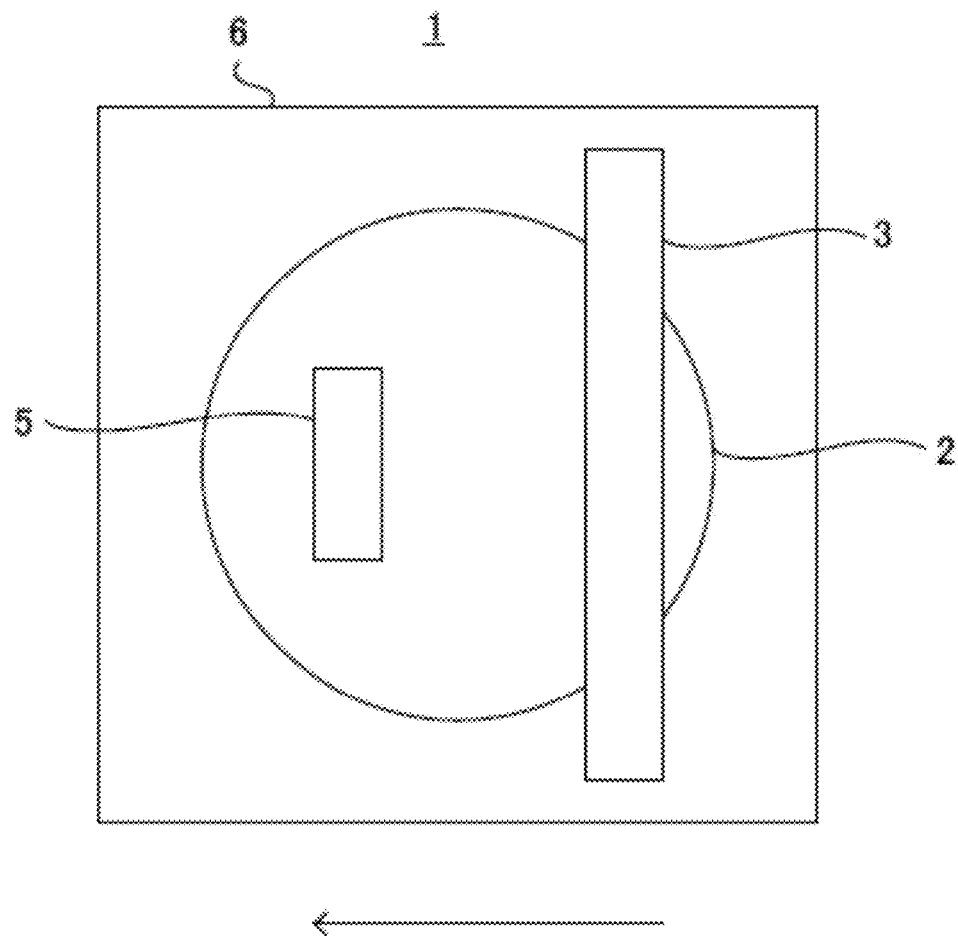
FIG. 1B is a top view schematically showing the structure of the wafer inspection apparatus relating to the one embodiment.

As shown in FIGS. 1A and 1B, a wafer inspection apparatus 1 (hereinafter, may be simply referred to as "the inspection apparatus 1") includes a light source. The light source is, for example, a light emitter 3 configured to emit light onto a to-be-inspected surface 2a of a wafer 2, which is a target to be inspected. The light emitter 3 may be positioned at such a distance from the to-be-inspected surface 2a that the light incident on the to-be-inspected surface 2a is approximately parallel light beams as well as at a shortest possible distance from the to-be-inspected surface 2a. For example, the light emitter 3 may be positioned in such a manner that the length of the optical axis is no less than 30 cm and no more than 2 m between the light source and the to-be-inspected surface 2a. The light emitter 3 may be, for example, a light source configured to emit ribbon-like (linear ribbon-like) light (a line light source). The light emitter 3 may be configured to emit ribbon-like light longer than the maximum length of the to-be-inspected surface 2a (the diameter of the wafer 2). The light emitter 3 can be formed by using a fluorescent or LED fluorescent lamp, for example.

(Imaging Unit)

Figure 2A:
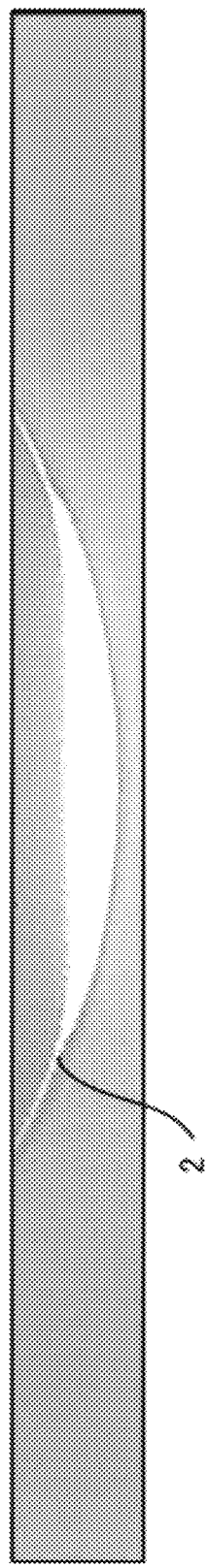
FIG. 2A shows an exemplary captured image obtained by an imaging unit included in the wafer inspection apparatus relating to the one embodiment.
Figure 2B:
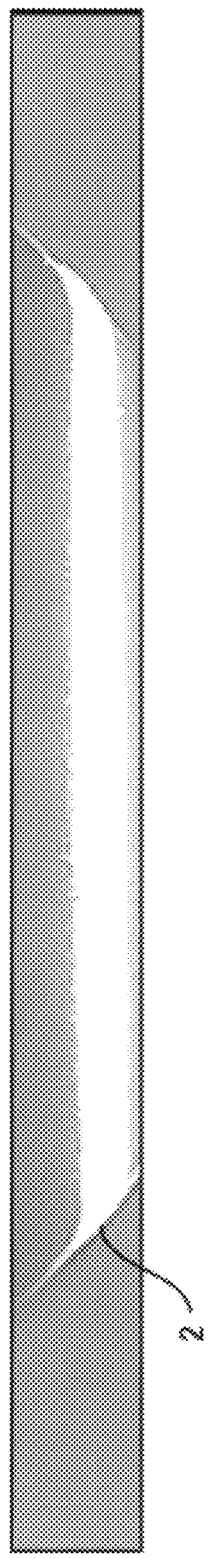
FIG. 2B shows an exemplary captured image obtained by the imaging unit included in the wafer inspection apparatus relating to the one embodiment.
Figure 2C:
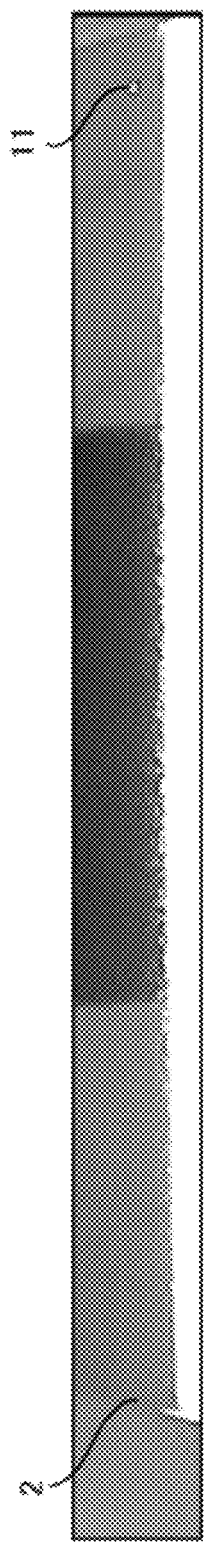
FIG. 2C shows an exemplary captured image obtained by the imaging unit included in the wafer inspection apparatus relating to the one embodiment.

The inspection apparatus 1 includes an imaging unit 5 configured to obtain or capture an image formed by the light that is emitted from the light emitter 3 and reflected by the to-be-inspected surface 2a. The imaging unit 5 may be configured to obtain an image including the outline of the image formed by the light that is emitted from the light emitter 3 and reflected by the to-be-inspected surface 2a (hereinafter, may be simply referred to as "the outline") and the region outside the outline, as shown in FIGS. 2A to 2C, for example. The imaging unit 5 may be positioned at such a distance from the to-be-inspected surface 2a that the image formed by the light that is emitted from the light emitter 3 and reflected by the to-be-inspected surface 2a (i.e., the reflected image formed by the light from the light emitter 3) can be captured as substantially parallel light as well as at a shortest possible distance from the to-be-inspected surface 2a. For example, the imaging unit 5 may be at a distance of no less than 30 cm and no more than 2 m from the to-be-inspected surface 2a. The imaging unit 5 may be a two-dimensional imaging element configured to obtain a two-dimensional image of the region outside the outline of the image formed by the light that is emitted from the light emitter 3 and reflected by the to-be-inspected surface 2a. The two-dimensional imaging element may be a digital camera, for example. The imaging unit 5 is electrically connected to a control unit 10, which will be described later. The imaging unit 5 transmits the obtained image (i.e., the captured image) to the control unit 10.

(Moving Unit)

As shown in FIGS. 1A and 1B, the inspection apparatus 1 includes a wafer moving mechanism 6. The wafer moving mechanism 6 is shown as an exemplary moving unit configured to move the to-be-inspected position on the to-be-inspected surface 2a by controlling the position of the wafer 2. In other words, the wafer moving mechanism 6 moves the to-be-inspected position on the to-be-inspected surface 2a by changing the relative positions of the wafer 2 and the light emitter 3. The wafer moving mechanism 6 may be configured to move the wafer 2 in, for example, a horizontal direction (for example, to the left and right on the paper on which FIG. 1A or 1B is shown). The wafer moving mechanism 6 is electrically connected to the control unit 10, which will be described later.

(Control Unit)

The inspection apparatus 1 includes the control unit 10. The control unit 10 performs operations necessary to conduct inspection on the to-be-inspected surface 2a. The control unit 10 may be realized by using a computer apparatus executing a predetermined program. In other words, the control unit 10 is configured as a computer including a combination of central processing unit (CPU), random access memory (RAM) and/or a storage device such as hard disk drive (HDD). A single computer apparatus may be used or a plurality of computer apparatuses may be used which are connected via a communication line. When a plurality of computer apparatuses are used, the capabilities of the respective components described later may be distributed among the plurality of computer apparatuses.

The control unit 10 is connected to an information output unit, for example, a display or the like. The information output unit allows the captured image received by the control unit 10 from the imaging unit 5 and the information regarding the results of the inspection performed by the control unit 10 to be output and displayed.

The control unit 10 includes an inspecting unit and an image processing unit. The control unit 10 reads and executes the program stored in the storage device to realize the inspection capability of the inspecting unit, the image processing capability of the image processing unit, and the like.

(Inspecting Unit)

When the control unit 10 receives the captured image from the imaging unit 5, the inspecting unit conducts inspection on the to-be-inspected surface 2a. Specifically speaking, the inspecting unit inspects whether there are defects on the to-be-inspected surface 2a by detecting, from the captured image transmitted from the imaging unit 5, an image 11 (see FIG. 2C) formed outside the outline of the image formed by the light that is emitted from the light emitter 3.

Figure 3:
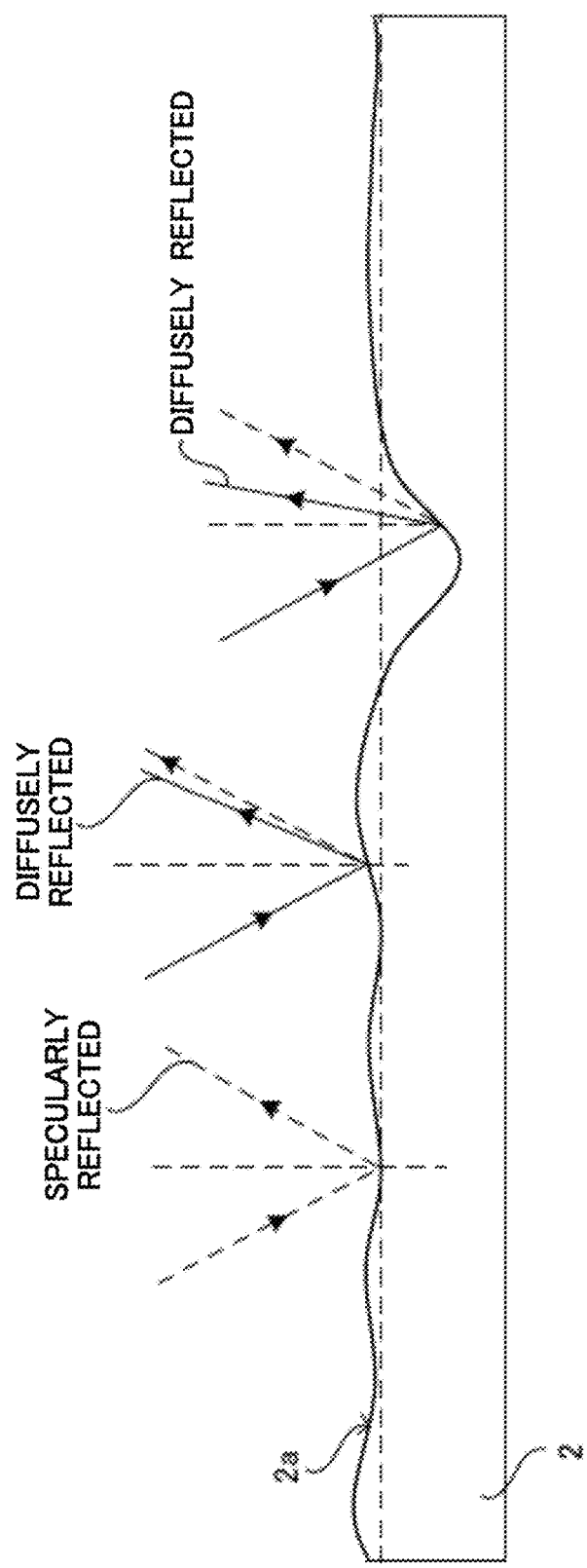
FIG. 3 illustrates how the light emitted from a light emitter included in the wafer inspection apparatus relating to the one embodiment is reflected on a to-be-inspected surface of a wafer.

A defect-free location on the to-be-inspected surface 2a specularly reflects the light emitted from the light emitter 3 as shown by, for example, the dotted lines in FIG. 3. In contrast to this, a defect (i.e., a depression or projection) on the to-be-inspected surface 2a scatters (i.e., diffusely reflects) the light emitted from the light emitter 3 as shown by, for example, the solid lines in FIG. 3. The diffusely reflected light forms an image away from the outline of the image formed by the light that is emitted from the light emitter 3. That is to say, a bright region is present in the region that is positioned outside the outline of the image formed by the light that is emitted from the light emitter 3 and supposed to be dark. In the following, the image formed by the light that is emitted from the light emitter 3 and scattered by the defect may be referred to as a scatter image. As the size of the defect formed on the to-be-inspected surface 2a increases (for example, as the depth of the depression or the height of the projection increases), the gradient of the side surface of the defect increases. Accordingly, the distance of the scatter image from the outline of the image formed by the light that is emitted from the light emitter 3 increases. Here, the side surface of the defect indicates the inward side surface of the depression or the outward side surface of the projection.

The inspecting unit detects, from the captured image, such a scatter image, i.e., a scatter image 11 that is positioned outside the outline of the image formed by the light that is emitted from the light emitter 3. For example, the inspecting unit may detect the scatter image 11 that is positioned outside the outline of the image formed by the light that is emitted from the light emitter 3 but within a region defined to detect the scatter image 11 (hereinafter, may be referred to as "detection target region"). The detection target region may be within a predetermined distance (for example, 4 mm) from the outline. More preferably, the detection target region is a region having a predetermined width (for example, 2 mm) outwardly relative to the outline, from the line that is parallel to the outline and distant by a predetermined distance (for example, 2 mm) from the outline. Here, the region in which an attempt is made to detect the scatter image 11 (in other words, the distance from the outline) can be changed as appropriate according to the distance between the wafer 2 and the light emitter 3, the distance between the wafer 2 and the imaging unit 5, the angle formed between the optical axis of the light emitter 3 and the optical axis of the imaging unit 5 (i.e., the imaging axis) (for example, 0 to 90 degrees) and/or the size of the defect to be detected, etc.

The inspecting unit approximates by a polynomial the outline of the image formed by the light that is emitted from the light emitter 3 and uses the line represented by the polynomial as the outline. In other words, the inspecting unit approximates by a second-, third- or higher order polynomial the shape of the outline of the image formed by the light that is emitted from the light emitter 3. If a straight-line line light source is used as the light emitter 3, no depressions or projections or other defects are formed on the to-be-inspected surface 2a, and the to-be-inspected surface 2a is perfectly planar (in other words, a flat surface), the image formed by the light that is emitted from the light emitter 3 and reflected by the to-be-inspected surface 2a has an outline shaped as a straight line. In other words, the outline of the image formed by the light that is emitted from the light emitter 3 can be represented by a first-order equation. However, the wafer 2 has been normally subjected to a variety of treatments such as deposition. As a result of the treatments, the to-be-inspected surface 2a of the wafer 2 is not a perfectly flat surface. For example, the to-be-inspected surface 2a is deformed to have concentric depressions and/or projections, and/or to be shaped like a saddle. Therefore, even if a straight-line line light source is used as the light emitter 3, the image formed by the light that is emitted from the light emitter 3 and reflected by the to-be-inspected surface 2a has a curved outline. For example, if the wafer 2 is deformed to have concentric depressions or projections, the inspecting unit can approximate by a simple second-order polynomial the outline of the image formed by the light that is emitted from the light emitter 3 and reflected by the to-be-inspected surface 2a. As another example, if the outer edge of the wafer 2 is deformed because a cutting blade is pushed into the wafer 2 to cut the wafer 2 into a predetermined shape using the cutting blade (in other words, if the outer edge of the wafer 2 has a sag), the outline of the image formed by the light that is emitted from the light emitter 3 and reflected by the to-be-inspected surface 2a has a more complex shape but can be still approximated by a polynomial. In other words, the inspecting unit can approximate by a polynomial the outline of the image formed by the light that is emitted from the light emitter 3.

If the wafer 2 is deformed to have concentric depressions or projections having a fixed curvature are formed, moving the to-be-inspected position on the to-be-inspected surface 2 causes the outline of the image formed by the light that is emitted from the light emitter 3 to translate. Accordingly, the same polynomial can be applied to all of the outlines of the images formed by the light that is emitted from the light emitter 3 that can be obtained by moving the to-be-inspected position on the to-be-inspected surface 2a. In other words, the inspecting unit only approximates by a polynomial the shape of the single outline that passes through the position closest to the center of the to-be-inspected surface 2a (for example, the outline passing through the center of the wafer 2, which may be hereinafter referred to as "the center outline"). The inspecting unit approximates the outlines of the images formed by the light that is emitted from the light emitter 3 and reflected by the other portions on the to-be-inspected surface 2a by the polynomial used to approximate the center outline on the to-be-inspected surface 2a. For example, the inspecting unit obtains the image, formed by the light that is emitted from the light emitter 3, that includes the outline passing through the position closest to the center of the to-be-inspected surface 2a and approximates the outline included in the obtained image by a polynomial. In the above-described manner, the computation is reduced and the inspection can be conducted at an improved rate (i.e., the processing rate can be improved).

(Image Processing Unit)

Figure 4:
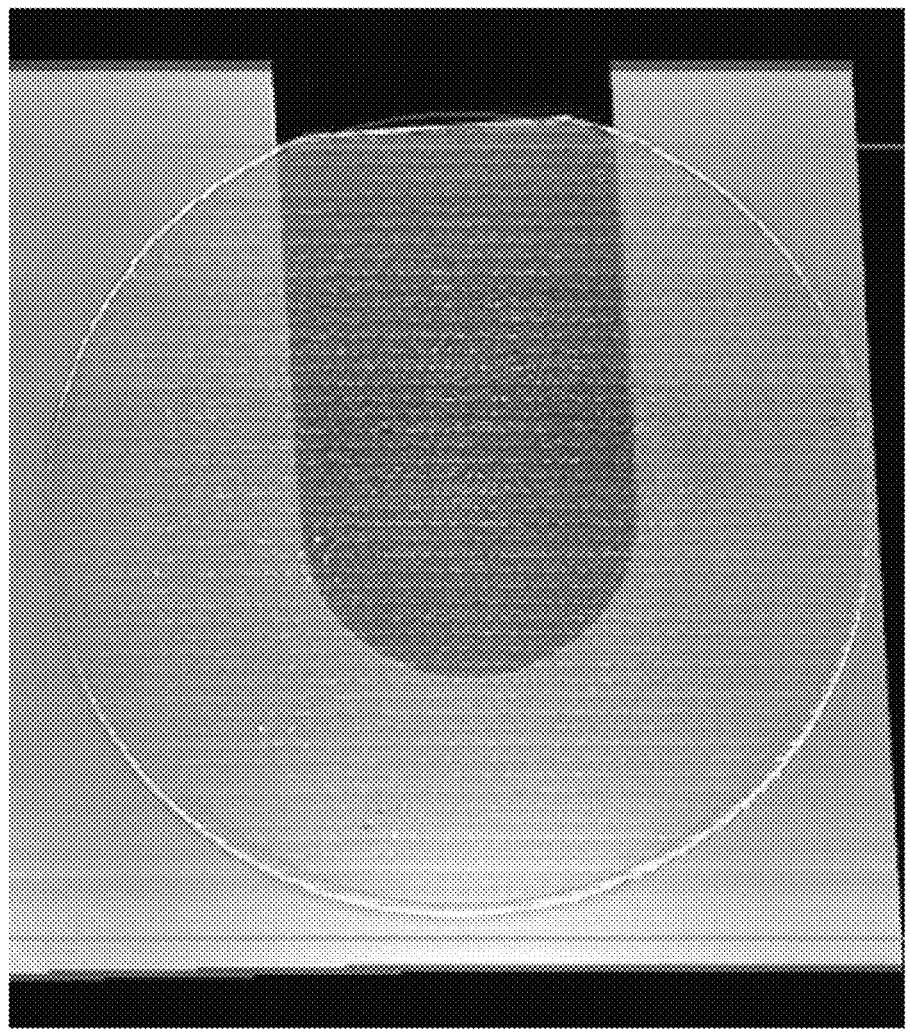
FIG. 4 shows an exemplary image generated by a control unit included in the wafer inspection apparatus relating to the one embodiment.
Figure 5:
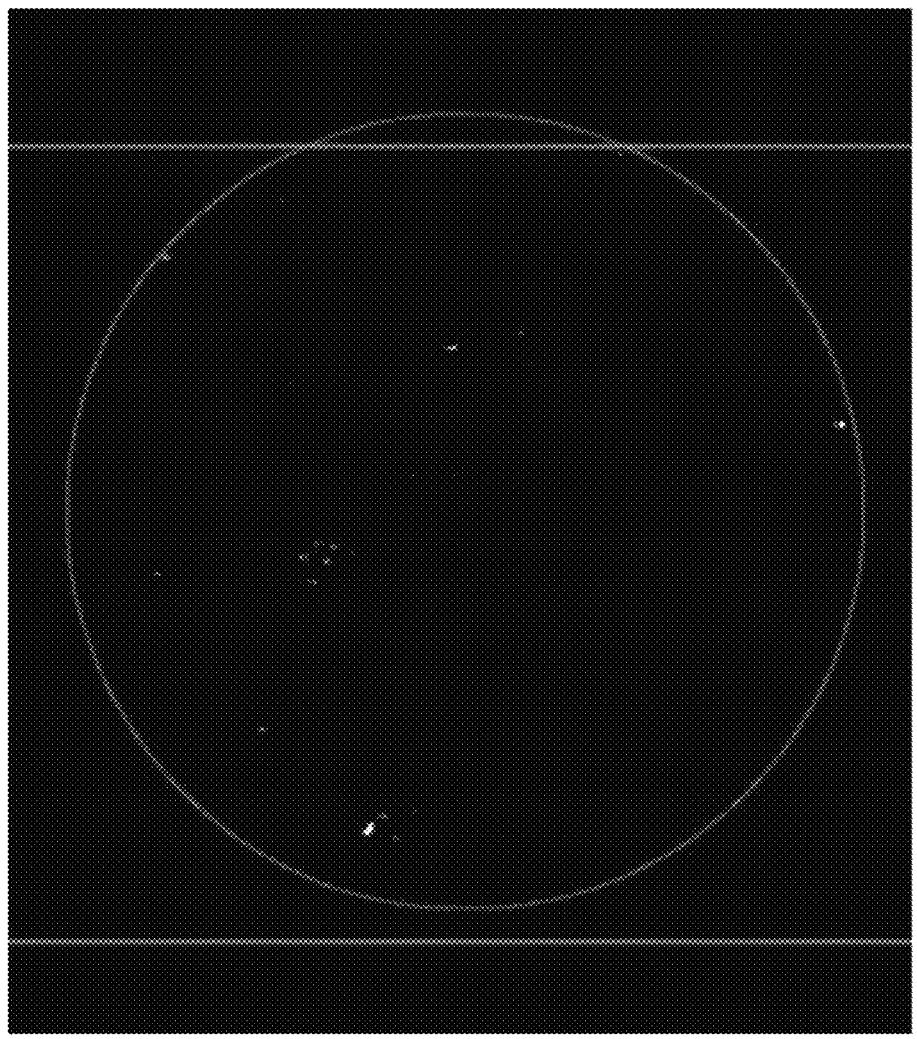
FIG. 5 shows an exemplary image generated by the control unit included in the wafer inspection apparatus relating to the one embodiment.

The image processing unit obtains the images of the individual inspection target positions on the to-be-inspected surface 2a captured by the imaging unit 5. The obtained images each include the outline of the image formed by the light that is emitted from the light emitter 3 and reflected by the to-be-inspected surface 2a and the region outside the outline. The image processing unit connects together, from the obtained images, the images of the detection target regions outside the outlines. In this manner, the image processing unit generates a collection image of the entire to-be-inspected surface 2a as shown in FIG. 4, for example. In addition, the image processing unit detects the scatter image 11 formed within the collection image and binarizes the collection image by differentiating the detected scatter image 11 and other portions to generate a binarized image as shown in FIG. 5, for example.

(2) Inspection Method

The following describes the method of inspecting the wafer 2, which is an object to be inspected, using the above-described inspection apparatus 1.

(Image Obtaining Step)

To start with, the wafer 2 is placed on the wafer moving mechanism 6, which serves as a moving unit. Subsequently, the light emitter 3 emits light onto the to-be-inspected surface 2a. Following this, the imaging unit 5 captures the image formed by the light that is emitted from the light emitter 3 and reflected by the to-be-inspected surface 2a. Specifically speaking, the imaging unit 5 captures and obtains the image containing the outline of the image formed by the light that is emitted from the light emitter 3 and reflected by the to-be-inspected surface 2a and the region outside the outline. The imaging unit 5 transmits the captured image to the inspecting unit.

(Moving Step)

After the completion of the image obtaining step, the wafer moving mechanism 6 moves the wafer 2 by a predetermined amount in a predetermined direction in order to move the to-be-inspected position on the to-be-inspected surface 2a. For example, the wafer moving mechanism 6 moves the wafer 2 in a horizontal direction (for example, the left direction on the paper showing FIGS. 1A and 1B) to change the relative positions of the wafer 2 and the light emitter 3. As a result, the to-be-inspected position on the to-be-inspected surface 2a is moved by a predetermined amount.

(Repeating Step)

Until the entire to-be-inspected surface 2a is inspected, the image obtaining step and the moving step are alternately and repeatedly performed.

(Inspecting Step)

On reception of the captured images of the entire to-be-inspected surface 2a from the imaging unit 5, the inspecting unit conducts inspection by detecting from the captured images the scatter image 11 formed outside the outline of the image formed by the light that is emitted from the light emitter 3. More specifically, the inspecting unit first obtains the image formed by the light that is emitted from the light emitter 3 that contains the center outline. After this, the inspecting unit approximates by a polynomial the outline in the obtained image formed by the light that is emitted from the light emitter 3. The line resulting from the polynomial approximation is now treated as the outline. The outlines of the images formed by the light that is emitted from the light emitter 3 and reflected at other positions on the same to-be-inspected surface 2a are each treated as a line having the same shape as the center outline and approximated by the same polynomial as the center outline. The inspecting unit then detects, from the images captured by the imaging unit 5, the scatter image 11 formed within a detection target region that is defined outside the outline of the image formed by the light that is emitted from the light emitter 3 and to detect (extract) the scatter image 11, and inspects whether there are any defects on the to-be-inspected surface 2a. For example, the inspecting unit detects the scatter image 11 that is formed within the detection target region. The detection target region is positioned outside the outline of the image formed by the light that is emitted from the light emitter 3 and has a predetermined width (for example, 2 mm) outwardly relative to the outline from the line that is parallel to the outline and distant by a predetermined distance (for example, 2 mm) from the outline of the image formed by the light that is emitted from the light emitter 3.

(Image Processing Step)

On completion of the inspection of the entire to-be-inspected surface 2a, the image processing unit connects together, from among the images of the respective inspection target positions on the to-be-inspected surface 2a that are captured by the imaging unit 5 and each contain the outline of the image formed by the light that is emitted from the light emitter 3 and the region outside the outline, the images of the detection target regions outside the outlines. In this way, the image processing unit generates a collection image from the captured images of the entire to-be-inspected surface 2a. In addition to generating the collection image, the image processing unit detects the scatter image 11 formed within the collection image and binarizes the collection image by differentiating the detected scatter image 11 and the other portions to generate a binarized image.

(3) Effects Produced by the Present Embodiment

The present embodiment can produce the following one or more effects.

(a) According to the present embodiment, the light emitter 3 emits light onto the to-be-inspected surface 2a, the imaging unit 5 captures and obtains the image formed by the light that is emitted from the light emitter 3 and reflected by the to-be-inspected surface 2a, and detects the scatter image 11 formed outside the outline of the image formed by the light that is emitted from the light emitter 3 and reflected by the to-be-inspected surface 2a. In this way, the to-be-inspected surface 2a is inspected. With such a configuration, the wafer 2 can be inspected accurately within a short period of time.

In addition, the inspection apparatus 1 relating to the present embodiment can accurately inspect the to-be-inspected surface 2a without a large-scale optical system of great complexity. In other words, the simple and small-sized inspection apparatus 1 can accurately inspect the wafer 2. In addition, since the inspection apparatus 1 can inspect the to-be-inspected surface 2a without using a light source of emitting laser light as the light emitter 3, the inspection apparatus 1 can be manufactured at low cost.

(b) As being configured to detect the scatter image 11 formed in the region that is outside the outline of the image formed by the light that is emitted from the light emitter 3 and reflected by the to-be-inspected surface 2a and positioned within a predetermined distance from the outline, the inspection apparatus 1 can detect defects that have a predetermined size (for example, depressions having a depth of or projections having a height of several hundred nanometers or more) on the to-be-inspected surface 2a. For example, when a predetermined film is deposited on the wafer 2, the inspection apparatus 1 can detect defects caused by the deposition conditions such as particles (i.e., garbage) within a processing furnace included in the apparatus used to deposit the predetermined film. In particular, the inspection apparatus 1 can detect defects having a size on the order of no less than several hundred nanometers and of μm scale by detecting the scatter image 11 formed within the detection target region having a width of 2 mm outwardly relative to the outline from the line that is distant by 2 mm from the outline and parallel to the outline. As is apparent from the above, the present embodiment is especially useful when it is desired to detect defects having a size of several hundred nanometers or more.

(c) The wafer moving mechanism 6 controls the position of the wafer 2 to move the to-be-inspected position on the to-be-inspected surface 2a. In this way, the entire to-be-inspected surface 2a can be inspected. For example, in order to inspect the entire to-be-inspected surface 2a, it is sufficient to move the wafer 2 in the horizontal direction using the wafer moving mechanism 6. Stated differently, the entire to-be-inspected surface 2a can be accurately inspected within a short period of time.

(d) Since the imaging unit 5 obtains the images containing the outline of the image formed by the light that is emitted from the light emitter 3 and the region outside the outline, the inspection apparatus 1 can obtain at the same time the image formed by the light emitted from the light emitter 3 and scattered by the defects (for example, the scatter image 11) and the image formed by the light emitted from the light emitter 3 and scattered by the recesses and rises smaller than the defects (for example, micro recesses and rises of approximately several dozen nanometers). In other words, the inspection apparatus 1 can simultaneously conduct inspection as to whether there are defects on the to-be-inspected surface 2a and inspection (for example, evaluation) for the surface roughness of the to-be-inspected surface 2a.

The surface roughness of the to-be-inspected surface 2a can be inspected by inspecting the outline of the image formed by the light that is emitted from the light emitter 3 and reflected by the to-be-inspected surface 2a. The micro recesses and rises smaller than the defects include recesses having a smaller depth than the defects or rises having a smaller height than the defects. Accordingly, the inward surfaces of the recesses or the outward surfaces of the rises have a smaller gradient than the defects. Therefore, the light scattered by the micro recesses and rises smaller than the defects are observed at positions closer to the outlines. In addition, the micro recesses and rises smaller than the defects also have a small surface area. Therefore, the images resulting from the micro recesses and rises are not very bright or do not have high contrast suitable for binarization unlike the images resulting from the defects (for example, the scatter image 11). Rather, the light diffusely reflected by the micro recesses and rises smaller than the defects only result in a random change in brightness in the region closer to the outline of the image formed by the light that is emitted from the light emitter 3. However, the degree of the change in brightness in the region closer to the outline reflects the surface roughness of the to-be-inspected surface 2a. Therefore, the surface roughness of the to-be-inspected surface 2a can be evaluated by obtaining the image near the outline (for example, within 2 mm from the outline) that is formed by the light emitted from the light emitter 3 and scattered by the micro recesses and rises smaller than the defects and then examining the brightness distribution within the image. As the degree of the brightness distribution decreases, the value of the surface roughness decreases and the flatness of the to-be-inspected surface 2a can be evaluated to increase.

(e) By using a line light source as the light emitter 3, which is configured to emit ribbon-like light longer than the maximum length of the to-be-inspected surface 2a (for example, the diameter of the wafer 2), the above-described effect (a) can improve. For example, the entire to-be-inspected surface 2a can be inspected simply by moving the wafer 2 from one of the ends of the straight line passing through the center of the wafer 2 to the other end. Accordingly, the inspection of the entire to-be-inspected surface 2a can be completed within approximately several dozen seconds.

(f) By using a two-dimensional imaging element as the imaging unit 5, the to-be-inspected surface 2a can be accurately inspected even if the wafer 2 has bowing (i.e., the wafer 2 is warped). In addition, software can be used to automatically identify the position of the outline within the two-dimensional images. As a result, the inspection is less influenced by a slight shift of the position of the light emitter 3 from a predetermined position.

(g) Since the image processing unit can generate the binarized image as shown in FIG. 5, for example, it becomes easy to know the positions and sizes of the defects on the to-be-inspected surface 2a.

(Other Embodiments of the Present Invention)

One embodiment of the present invention has been specifically described. The present invention, however, is not limited to the above-described embodiment, which can be modified as appropriate within the scope of the present invention.

According to the above-described embodiment, the wafer moving mechanism 6 is used to move the position of the wafer 2 for the purpose of moving the to-be-inspected position on the to-be-inspected surface 2a. The present invention, however, is not limited to such. Specifically speaking, the to-be-inspected position on the to-be-inspected surface 2a may be moved by controlling the position to which the light is emitted from the light emitter 3. Alternatively, the to-be-inspected position on the to-be-inspected surface 2a may be moved by controlling the position to which the light is emitted from the light emitter 3 and the position of the wafer 2.

According to the above-described embodiment, the control unit 10 is electrically connected to the wafer moving mechanism 6 to allow the control unit 10 to control the movement of the wafer moving mechanism 6. The present invention, however, is not limited to such. For example, the wafer moving mechanism 6 may be manually moved.

According to the above-descried embodiment, the image that is formed by the light emitted from the light emitter 3 and that includes the outline passing through the closest position to the center of the to-be-inspected surface 2a is obtained, the shape of the outline of only this image formed by the light emitted from the light emitter 3 is approximated by a polynomial, and the outlines of the other images formed by the light that is emitted from the light emitter 3 and reflected on the other positions on the to-be-inspected surface 2a are assumed to be a curved line having the same shape as the outline passing through the closest position to the center of the to-be-inspected surface 2a. The present invention, however, is not limited to such. For example, polynomial approximation may be performed on the outline of each of the images formed by the light emitted from the light emitter 3 and reflected on the respective inspection target positions on the to-be-inspected surface 2a.

Figure 6:
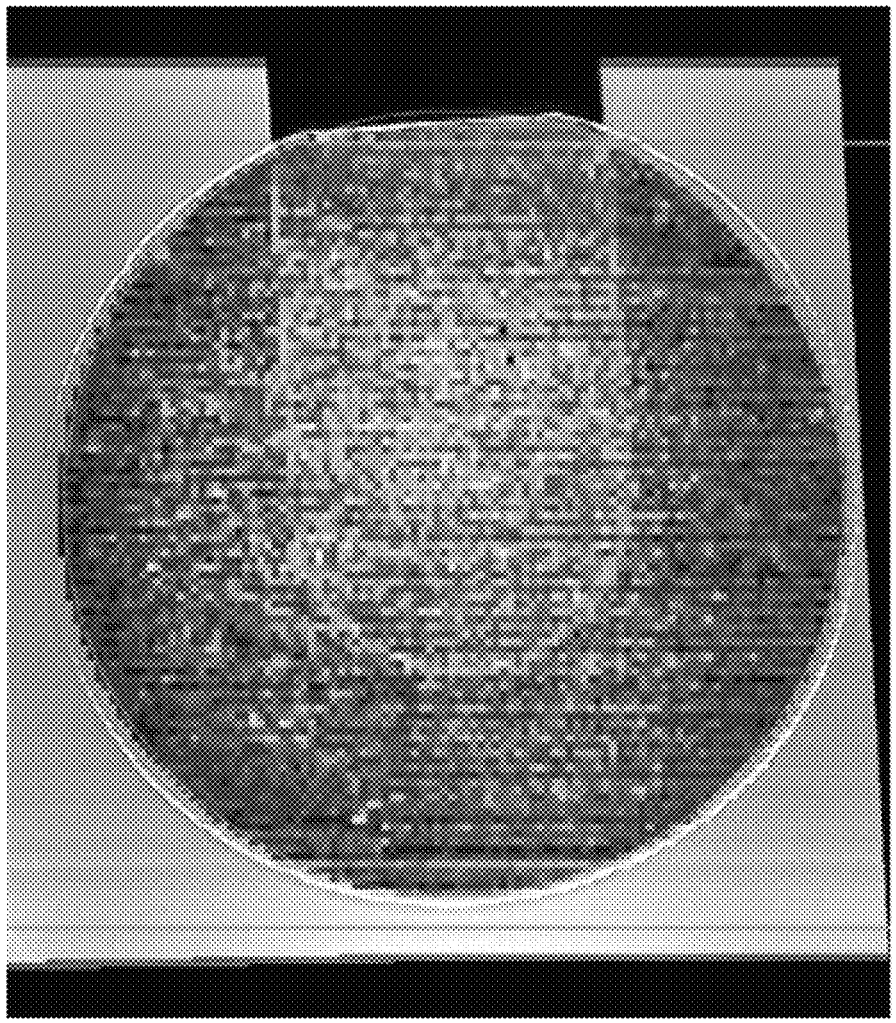
FIG. 6 shows an exemplary image generated by a control unit included in a wafer inspection apparatus relating to another embodiment.

The image processing unit may be configured to add up the brightness values of each pixel to generate an image in which different colors are used in the pixels depending on their total brightness values as shown in, for example, FIG. 6. This makes it possible to easily understand the surface roughness of the to-be-inspected surface 2a.

According to the above-described embodiment, the inspecting step is performed after the step of obtaining the image formed by the light emitted from the light emitter 3 is performed across the entire to-be-inspected surface 2a. The present invention, however, is not limited to such. For example, after the scatter image 11 is detected in the image formed by the light that is emitted from the light emitter 3 and reflected on a predetermined position on the to-be-inspected surface 2a, the to-be-inspected position on the to-be-inspected surface 2a may be moved. Alternatively, after the image formed by the light that is emitted from the light emitter 3 and reflected on a predetermined position on the to-be-inspected surface 2a is obtained, the scatter image 11 that is positioned outside the outline of the image formed by the light that is emitted from the light emitter 3 may be detected while the to-be-inspected position on the to-be-inspected surface 2a is being moved.

According to the above-described embodiment, the image processing step is performed. The image processing step, however, may not be performed.

According to the above-described embodiment, the imaging unit 5 is configured as a two-dimensional imaging element. The present invention, however, is not limited to such. For example, if the wafer 2 is not warped, the imaging unit 5 may be configured with a one-dimensional imaging element (for example, a line camera) that may obtain one-dimensional images formed by the light emitted from the light emitter 3 and reflected by the to-be-inspected surface 2a. If the wafer 2 is warped, however, the use of such a one-dimensional imaging element may inhibit accurate inspection of the wafer 2. To be specific, since the image formed by the light that is emitted from the light emitter 3 and reflected by the to-be-inspected surface 2a is warped, the outline of the image formed by the light that is emitted from the light emitter 3 is also warped. Therefore, in the scatter image detected from the image that is formed by the light emitted from the light emitter 3 and reflected by the to-be-inspected surface 2a and is obtained using the one-dimensional imaging element, the distance from the outline may be different in association with each of the elements constituting the array included in the one-dimensional imaging element. This may make it difficult to accurately locate the defects on the to-be-inspected surface. In addition, the information regarding the defects may not be accurately distinguished from the information regarding the micro recesses and rises smaller than the defects. Furthermore, if the position of the light source is shifted for some reason, the obtained images may be meaningless.

<Preferable Aspects of the Present Invention>

The following additionally notes the preferable aspects of the present invention.

<Additional Note 1>

One aspect of the present invention provides a wafer inspection apparatus including:

a light emitter configured to emit light onto a to-be-inspected surface of a wafer;

an imaging unit configured to obtain an image formed by the light emitted from the light emitter and reflected by the to-be-inspected surface;

a moving unit configured to move a to-be-inspected position on the to-be-inspected surface by controlling a position of one of the wafer and the light emitter; and an inspecting unit configured to inspect the to-be-inspected surface by detecting a scatter image formed by the light that is emitted from the light emitter and scattered by a defect of the to-be-inspected surface, the scatter image being formed outside an outline of the image formed by the light emitted from the light emitter.

<Additional Note 2>

According to the wafer inspection apparatus of Additional Note 1, the imaging unit preferably obtains the image containing the outline and a region outside the outline.

<Additional Note 3>

According to the wafer inspection apparatus of Additional Note 1 or 2, the inspecting unit preferably detects the scatter image that is formed within a predetermined distance from the outline.

<Additional Note 4>

According to the wafer inspection apparatus of one of Additional Notes 1 to 3, the light emitter preferably includes a light source configured to emit ribbon-like light.

<Additional Note 5>

According to the wafer inspection apparatus of one of Additional Notes 1 to 4, the inspecting unit preferably detects the outline by approximating the outline by a polynomial.

<Additional Note 6>

According to the wafer inspection apparatus of one of Additional Notes 1 to 5, the imaging unit is preferably configured to capture a two-dimensional image of the region outside the outline.

<Additional Note 7>

The wafer inspection apparatus of one of Additional Notes 1 to 6 preferably includes, as the moving unit, a wafer moving mechanism configured to move the wafer in a horizontal direction.

<Additional Note 8>

Another aspect of the present invention provides a wafer inspection method including causing a light emitter to emit light onto a to-be-inspected surface of a wafer and causing an imaging unit to obtain an image formed by the light emitted from the light emitter and reflected by the to-be-inspected surface, moving a to-be-inspected position on the to-be-inspected surface by controlling a position of one of the wafer and the light emitter, and inspecting the to-be-inspected surface by detecting a scatter image formed by the light that is emitted from the light emitter and scattered by a defect of the to-be-inspected surface, where the scatter image is formed outside an outline of the image formed by the light emitted from the light emitter. Here, the obtaining of the image and the moving are repeatedly performed until the entire to-be-inspected surface is inspected.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

DESCRIPTION OF REFERENCE NUMERALS

1 . . . inspection apparatus
2 . . . wafer
2a . . . to-be-inspected surface
3 . . . light emitter
5 . . . imaging unit
6 . . . moving unit (wafer moving mechanism)

What is claimed is:

1. A wafer inspection apparatus comprising:
a light emitter configured to emit light onto a to-be-inspected surface of a wafer;
an imaging unit configured to obtain a captured image, in which (i) an outline of an image formed by the light emitted from the light emitter and specularly reflected by the to-be-inspected surface and (ii) a region outside the outline are included;
a moving unit configured to move a to-be-inspected position on the to-be-inspected surface by controlling a position of one of the wafer and the light emitter; and
a processor configured to inspect the to-be-inspected surface by detecting, from the captured image, a scatter image formed by the light that is emitted from the light emitter and scattered by a defect of the to-be-inspected surface, the scatter image being formed in the region outside the outline, wherein the processor detects the scatter image that is formed within a predetermined distance from the outline.

2. A wafer inspection method comprising:
causing a light emitter to emit light onto a to-be-inspected surface of a wafer and causing an imaging unit to obtain a captured image, in which (i) an outline of an image formed by the light emitted from the light emitter and specularly reflected by the to-be-inspected surface and (ii) a region outside the outline are included;
moving a to-be-inspected position on the to-be-inspected surface by controlling a position of one of the wafer and the light emitter; and
inspecting the to-be-inspected surface by detecting, from the captured image, a scatter image formed by the light that is emitted from the light emitter and scattered by a defect of the to-be-inspected surface, the scatter image being formed in the region outside the outline, wherein the obtaining of the image and the moving are repeatedly performed until the entire to-be-inspected surface is inspected, and the inspecting detects the scatter image that is formed within a predetermined distance from the outline.

3. The wafer inspection apparatus as set forth in claim 1, wherein
the distance of the scatter image from the outline increases as the size of the defect formed on the to-be-inspected surface increases.

4. The wafer inspection apparatus as set forth in claim 1, wherein
the processor is configured to alternately and repeatedly perform obtaining the captured image and moving the to-be-inspected position until captured images of the entire to-be-inspected surface are obtained.

5. The wafer inspection apparatus as set forth in claim 4, wherein
the processor is further configured to generate a collection image of the entire to-be-inspected surface by connecting together scatter images of individual to-be-inspected positions on the to-be-inspected surface.

6. The wafer inspection apparatus as set forth in claim 1, wherein
the processor is configured to detect the scattered image formed within a region having a width of 2 mm outwardly relative to the outline from a line that is 2 mm away from the outline and parallel to the outline.

7. The wafer inspection apparatus as set forth in claim 1, wherein
the processor is further configured to evaluate surface roughness of the to-be-inspected surface by evaluating degree of change in brightness within a region between the outline and a line that is 2 mm away from the outline and parallel to the outline.

8. The wafer inspection apparatus as set forth in claim 7, wherein
the processor is configured to simultaneously conduct inspecting the to-be-inspected surface as to whether there is a defect on the to-be-inspected surface and evaluating the surface roughness of the to-be-inspected surface.

9. The wafer inspection apparatus as set forth in claim 1, wherein
the processor is configured to approximate the outline by a polynomial.

10. The wafer inspection apparatus as set forth in claim 1, wherein
the light emitter is configured to emit ribbon-like light longer than the maximum length of the to-be-inspected surface.

* * * * *